United States Patent
Michaeli

(10) Patent No.: US 6,740,793 B2
(45) Date of Patent: May 25, 2004

(54) TRANSGENIC ANIMAL HAVING A DISRUPTED PDE7A GENE AND USES THEREOF

(75) Inventor: Tamar Michaeli, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/950,920

(22) Filed: Sep. 12, 2001

(65) Prior Publication Data

US 2003/0115615 A1 Jun. 19, 2003

(51) Int. Cl.⁷ .................. A61K 67/027; C12N 15/00
(52) U.S. Cl. ............................ 800/18; 800/25

(58) Field of Search ...................... 800/18, 25

*Primary Examiner*—Anne-Marie Falk
*Assistant Examiner*—Celine Qian
(74) *Attorney, Agent, or Firm*—Amster, Rothstein & Ebenstein LLP

(57) ABSTRACT

The present invention provides a transgenic non-human animal whose genome comprises a disruption in its endogenous PDE7A gene, wherein the transgenic animal exhibits decreased expression of functional PDE7A protein relative to wild-type. The present invention further provides a method for creating a transgenic non-human animal exhibiting decreased expression of functional PDE7A protein relative to wild-type. Finally, the present invention provides a method for screening a PDE7A inhibitor for at least one side-effect.

14 Claims, 4 Drawing Sheets

Sequences used to generate the PDE7 KO:

PCR amplification of Lox/NEO/URA3/Lox

5' oligo         Intron/Exon 2             Exon 2/loxP
ATACTTTTTTTTTTTCAG<u>AGACGTGGAGCTATTTCCTA</u>AGAATTCCGATCATATTCAATAACC

R     R     G     A     I     S     Y

5'    Int1/Exon 2       ATACTTTTTTTTTTTCAG AGA CGT GGA GCT ATT TCC T<u>A</u> ter    EcoRI
Lox(oligo)      <u>A</u> G  <u>AA TTC</u> CGA TCA TAT TCA ATA ACC

Lox   CTT AAT <u>ATA ACT TCG TAT A</u>AT GTA TGC TAT ACG AAG TTA TTA

GGT CTG AAG AGG AGT TTA CGT CCA GCT GCG CAT AAA AAT CA

--------
                NEO-R---------URA3----------

3' Exon2/intron2
<u>ATA ACT TCG TAT A</u>AT GTA TGC TAT ACG AAG TTA TTA GGT CCA GCG GCC ter
CCC ACT GCG GTA TGC <u>TAG</u> GTA AGT ACA ACT TTA TTG TTT TTA TTA AAT TTA TG

3' oligo                                        intron2/exon2-----
CATAAATTTAATAAAAACAATAAAGTTGTACTTACCTAG<u>CATA</u>CCGCAGTGGGGGCCGCTGGACCTAA

3' oligo rev/comp                      --------exon2/ intron2 junction
TTAGGTCCAGCGGCCCCCACTGCGG<u>TATGC</u>TAGGTAAGTACAACTTTATTGTTTTTATTAAATTTATG

FIG. 2

Genomic sequences after popout of Lox/NEO/URA3

Cre product (exon seq and lox repeated seq in bold) after removal of the NEO -URA3 markers

```
                              ' '      R   R   G   A   I   S   Y

Int1/Exon 2  ATACTTTTTTTTTTTTCAG AGA CGT GGA GCT ATT TCC TA ter   EcoRI
Lox(oligo)      A G AA TTC CGA TCA TAT TCA ATA ACC Lox    CTT AAT ATA ACT TCG TAT AAT GTA TGC TAT ACG AAG TTA TTA GGT ' '        ter    '
CCA GCG GCC CCC ACT GCG GTA TGC TAG GTA AGT ACA ACT TTA TTG TTT
                          -M2-
TTA TTA AAT TTA TG
```

Cre product seq
ATACTTTTTTTTTTTTCAG AGA CGT GGA GCT ATT TCC TA A G AA TTC CGA TCA TAT TCA ATA ACC CTT AAT ATA ACT TCG TAT AAT GTA TGC TAT ACG AAG TTA TTA GGT CCA GCG GCC CCC AC T GCG GTA TGC TAG GTA AGT ACA ACT TTA TTG TTT TTA TTA AAT TTA TG
Cre product is -32bp+96bp= +64bp longer than normally excised exon 2

FIG. 3

PDE7 Exon2 and flanking sequences

A

GCCGTGGATCTGAGAGCATGGGTTTGGAACTCACTTCCCAGACAGTGGGACCACTGGAGGACT
TGTGAGTGGGACCTGAAATAGCCACTCCTCTAAGGCCTGGGGCTTGGGGAAGATGCACNTGAA
CCATCAACAGATTGGCCTTTCCCCTCTCGTTCCCTTTGAGTAACTCTTGCGATTGTTTTAGAAA
CCAACTTCGGTGGGGCTGGGGATACTGTGCCAAAGACTCCAGTTCCATCCTCAGCACCCCACT
CCACAGAAGAGATCAGCTGTGTGCCATCTCAGACGCTTCACTCCTGTGTCCTTTTCTTAGGAGT
TCTTAGCTAGGTTGTACCTGTTTGTCTCGTAGCTAGAGATTTCCAGAGCAGATGCATTTTGTAT
ATTCAACATTGTTTGGTGCAATATGCTGCAATTACATGTAATAATACAAGCATGTTCACTGAAT
TAAATTTTAGCTCACATTTCATTATCATGTACTGAAATATATACTTTTTTTTTTTCAGAGACGT
GGAGCTATTTCCTATGACAGTTCTGATCAGTCTGCGTTATATATTCGTATGCTAGGTAAGTACA
ACTTTATTGTTTTTATTAAATTTATGTATATGAGTTCACAGATGGTTGTGAGCCTTCACGTGGT
TGTTGGGAATTGAATTTAGGACCTCTGCTCACTCCAGTCAACTCCGCTCGCTCAGTCCCTACTT
GCTCAGGCCCAAAGATTTATTTATTATTATAAATAAGTACACTCTTGCTGTCTTCAGACGCACC
AGAAGAGGGTGTCAGATCTCATTATGGGTGGTTATGAACCACCATGTGGTTGCTAGGATTTGA
ACTCAGGACCTTCAGAAGAGCAGTCAGTGAGTGCTCTTTCCCACTGAGCCATCTCTCCAGCCC
CTAAGTAAAACTTTATACCAGTACCAGTTAGTCTTGCGGTTGTATTATCTGAGATGAGATATCT
TGCACTNAGGTACCTTTCACTACTTTTTGAAGCAGAAATTGAAGTTTAGCATCTGAAAACTAAT
ACTGAGTGTGATGAATAAAGAGAGGTATTTTAGAGTTAGGGCAATTTAAAAGTCTGGTTTAAT
AGGACAGTCTTTTAGGGGACAGCTTAGCTGTTTTAGAGCATTCTTTATGGAACATAGGTTAAAT
AGGTTTCTAACACTGCTAAAGGCCAACCAACTGCTAGTTAGCTGTGCATACCACAGTGTGTAA
AATGAATTATTTTAATATAAAATGTAAGTAATAAAATTAATCCAGCAGCTGNATTCCCTTTACC
TTTGCTAGTCCCCAGTAATCACACNGAGAATTCCAGACTTATTTCAAGCTTTCCCT

B

TACCCCGNACNGCANTTGCCTNCNGACNGTGANCAGCTGACTNTTNNGNGAATGCACTG
CCTGGCTAGCCNTNCTGCCCAGCGCATGCTTAATGCCACGACCTCACCACTAGTGCAAAG
CNNGAGAAANAGTACTGGAAGACAAGAAAAATCTAGCTTANAATCTCACAAAAGGTCTC
AGGCTAGCCCAAACATGCCTGTGATCTTTGTTCTACAGAGNNTTTTAAAACAATTATCAA
AAANGCTTGGCAAGGCTAAACATTTCCTCATCCTGCTCACGGAGGCCANTTTTGCAAGCA
TAATTGCCATTGCNCTCCNAAAATATTTGAACATTTTGCACTTTACCTCTGAGTATTGAAT
TTCTTTAAACTTTTGCTTTCTTCCAATATGGGATTACTTTATGACAACAGTGGCACGATAA
ATGTGATCTGTGCCATTNAAATACNTANGTAATTCATTCTAAATTTACTGACNAGGTCAT
GTATTANCACATAATAAAAGATATTTTGTTCTCNAGNCCTAAGAAAGTCTAAGGTCCTGT
AATATTANNGGTCCATGTCCTGTTCTTGCGACTGANCNGAATGANCTTGTCCANAAACAA
ANGNCTNTCCGTATCCCAACCTCTTACCTTCCATTGGNAACCCAAGCAAGTTACTTTTGAT
AAAAGAGCCTCTCACGAAACCTCTCAATCGAGAAGTTAGCAAATATGTTTTTAAACTCTA
TTACCCAGCANGCTCCATNTTAATGACAAANAATTNNCTAAAAAATCATAGTGATCCGNA
ACCTGGNTTCCTGCCCTTTATACAATTTTTNTTCCATATTAACCNAATGGTGCAACAAATN
CCAAATTGGCTTGAACGGGAAAAGGA

FIG. 4

TRANSGENIC ANIMAL HAVING A DISRUPTED PDE7A GENE AND USES THEREOF

FIELD OF THE INVENTION

The present invention is directed to transgenic non-human animals in which a cAMP phosphodiesterase is selectively inactivated. In particular, the non-human transgenic animals of the present invention contain a disrupted PDE7A gene, which results in abrogation of expression of wild-type PDE7A-encoded proteins. The transgenic animals of the present invention may exhibit reduced or no expression of PDE7A gene products, expression of mutant PDE7A gene products, or expression of only human PDE7A gene products (wild-type or mutant). The present invention is also directed to methods for making the transgenic animals of the present invention. Finally, the present invention is directed to methods for using these transgenic animals to screen therapeutic compounds and to modulate immune and other physiological responses.

BACKGROUND OF THE INVENTION

Cyclic AMP (cAMP) is a second messenger with broad physiological implications, including anti-proliferative effects in lymphoid and myeloid cells, endocrine cells, mammary cells, and prostate cells. In addition, reduced cAMP levels are associated with certain cancers (e.g., breast tumors, chronic lymphocytic leukemia (CLL), and prostate tumors), which may be treated with cAMP elevating agents.

Phosphodiesterases (PDEs) are enzymes, present in cells, that are important regulators of immune function. Lymphoid and myeloid cells contain multiple cyclic nucleotide PDEs that lower cAMP levels in response to antigenic stimulation, thereby promoting cell proliferation. For example, phosphodiesterase 7A (PDE7A) is proposed to be a critical regulator of lymphocyte proliferation, although in vivo data in this regard are lacking. PDE3, PDE4, and PDE7A are present in T cells. Each belongs to a different PDE family. These PDE families are related to each other, in that they share a 25% sequence similarity within their catalytic domains, but their regulatory domains are distinct. Selective inhibitors exist for the catalytic domains of particular PDE families. For example, sildenafil (Viagra™), an inhibitor of PDE5, is marketed for the treatment of erectile dysfunction. Selective inhibitors for PDE4 are immunosuppressant drugs in different stages of development. However, the wide tissue distribution of PDE4 isozymes leads to side-effects of PDE4 inhibitors, such as emesis. PDEs that are expressed in a tissue-selective manner, and that respond to specific-activating signals, are good targets for elevation of cAMP in specific physiological conditions.

Immunologic responses and immunodeficiency conditions (e.g., allergy; asthma; autoimmune disorders, such as Hashimoto's thyroiditis, systemic lupus erythematosus (SLE), Goodpasture's syndrome, Crohn's disease, pemphigus, receptor autoimmunity, Graves' disease, myasthenia gravis, insulin resistance, and autoimmune hemolytic anemia; chronic obstructive pulmonary disease (COPD); CLL; inflammation; and rheumatoid arthritis) are either caused by, or associated with, proliferation and/or accumulation of lymphoid cells. Inhibition of cAMP PDEs in lymphoid cells, though, can inhibit the antigen-stimulated proliferation of these cells. In particular, since PDE7A is a primary modulator of lymphocyte proliferation, it is believed to play a role in immunologic responses and immunodeficiency conditions such as those described above.

Phosphodiesterase inhibitors are currently being investigated for their potential to modulate immune function. For example, inhibitors have been developed which target PDE4—a phosphodiesterase known to affect lymphocyte proliferation. However, PDE4 inhibitors have been shown to have deleterious side-effects, such as severe emesis, that preclude their use clinically. Because of PDE7A's apparent role in immunologic responses and immunodeficiency diseases, therapeutic strategies designed to inhibit PDE7A activity (by decreasing PDE7A levels and/or by reducing PDE7A activity) also have been proposed.

Current mice models for immunodeficiency diseases and for immune responses to allergens, antigens, superantigens, and transplanted tissues all express PDE7A. Furthermore, to date, the study of PDE7A function, particularly in muscle, has been hindered by the absence of selective inhibitors for this phosphodiesterase, the absence of cultured cell lines expressing the muscle PDE7A2 splice variant (including cultured myoblast cell lines like C2C12), and the absence of cell lines that can serve as bona fide physiological models for muscle function. Accordingly, the development of viable PDE7-knockout (PDE7KO) mice would allow a physiological determination of defects in PDE7A function, provide a source of control tissues for comparative analysis of PDE7A activity, and facilitate the identification of PDE7A inhibitors and the evaluation of their efficacy.

SUMMARY OF THE INVENTION

The present invention is directed to the development of novel transgenic non-human animals in which a cAMP phosphodiesterase has been selectively inactivated. Specifically, the inventor has produced a genetically-engineered mouse in which one of the PDEs, PDE7A, has been knocked out. This mouse expresses a reduced level of PDE7A-encoded proteins relative to the corresponding wild-type animal. The mouse also has significant immune defects that appear to be distinct from those seen in other PDE-knockout mice.

The transgenic mouse of the present invention will allow researchers to use convenient and well-studied small laboratory animals, including rats or mice, to study immune responses and other conditions and conditions associated with lymphoid cell proliferation. Because the transgenic mouse does not express endogenous PDE7A, it also can be used to study the long-term sequellae induced by treatment with drugs that inhibit PDE7A. Therefore, the invention will be useful for testing side-effects of compounds that inhibit PDE7A, and for screening candidate therapeutic compounds that block the proliferation of lymphoid and other immune cells.

Accordingly, the present invention provides a transgenic non-human animal whose genome comprises a disruption in its endogenous PDE7A gene, wherein the transgenic animal exhibits decreased expression of functional PDE7A protein relative to wild-type.

In addition, the present invention provides a method for creating a transgenic non-human animal exhibiting decreased expression of functional PDE7A protein relative to wild-type by: (a) generating a PDE7A targeting vector; (b) introducing the PDE7A targeting vector into a recipient cell of a non-human animal, to produce a treated recipient cell; (c) introducing the treated recipient cell into a blastocyst of a non-human animal, to produce a treated blastocyst; (d) introducing the treated blastocyst into a pseudopregnant non-human animal; (e) allowing the transplanted blastocyst to develop to term; (f) identifying a transgenic non-human animal whose genome comprises a disruption in its endogenous PDE7A gene; and (g) breeding the transgenic non-human animal to obtain a transgenic non-human animal exhibiting decreased expression of functional PDE7A protein relative to wild-type.

Finally, the present invention provides a method for screening a PDE7A inhibitor for at least one side-effect, by administering a PDE7A inhibitor to the transgenic non-human animal of the present invention, and detecting at least one side-effect, if any, of the PDE7A inhibitor in the transgenic animal.

Additional objects of the present invention will be apparent in view of the description which follows.

BRIEF DESCRIPTION OF THE FIGURES

FIG. 2 shows the sequences used to generate the PDE7KO. Depicted are a 5' oligonucleotide used for PCR amplification of Lox/NEO/URA3/Lox (SEQ ID NO:8), which includes 5' intron1/exon2 (nucleotides 1–39 of SEQ ID NO:8) and Lox(oligo) (nucleotides 40–64 of SEQ ID NO:8); a lox oligonucleotide used for PCR amplification of Lox/NEO/URA3/Lox (SEQ ID NO:9); a 3' oligonucleotide used for PCR amplification of Lox/NEO/URA3/Lox (SEQ ID NO:10); a 3' oligonucleotide containing intron2 and exon2, used for PCR amplification of Lox/NEO/URA3/Lox (SEQ ID NO:11); and a 3' oligonucleotide rev/comp (nucleotides 34–101 of SEQ ID NO:10).

FIG. 3 illustrates the genomic sequences after popout of Lox/NEO/URA3. Depicted are a 5' intron1/exon2 (nucleotides 1–39 of SEQ ID NO:8); a Lox(oligo) (nucleotides 40–64 of SEQ ID NO:8); a lox oligonucleotide after popout of Lox/NEO/URA3 (SEQ ID NO:12); and a nucleic acid sequence of PDE7A locus after Cre-recombinase-mediated removal of Lox/NEO/URA3 sequence (SEQ ID NO:13).

FIGS. 4A and 4B depict PDE7 exons and flanking sequences. FIG. 4A sets forth exon2 of PDE7A exon and flanking introns (SEQ ID NO:14), and FIG. 4B sets forth PDE7A muscle-specific exon (SEQ ID NO:15).

DETAILED DESCRIPTION OF THE INVENTION

Figure 1:
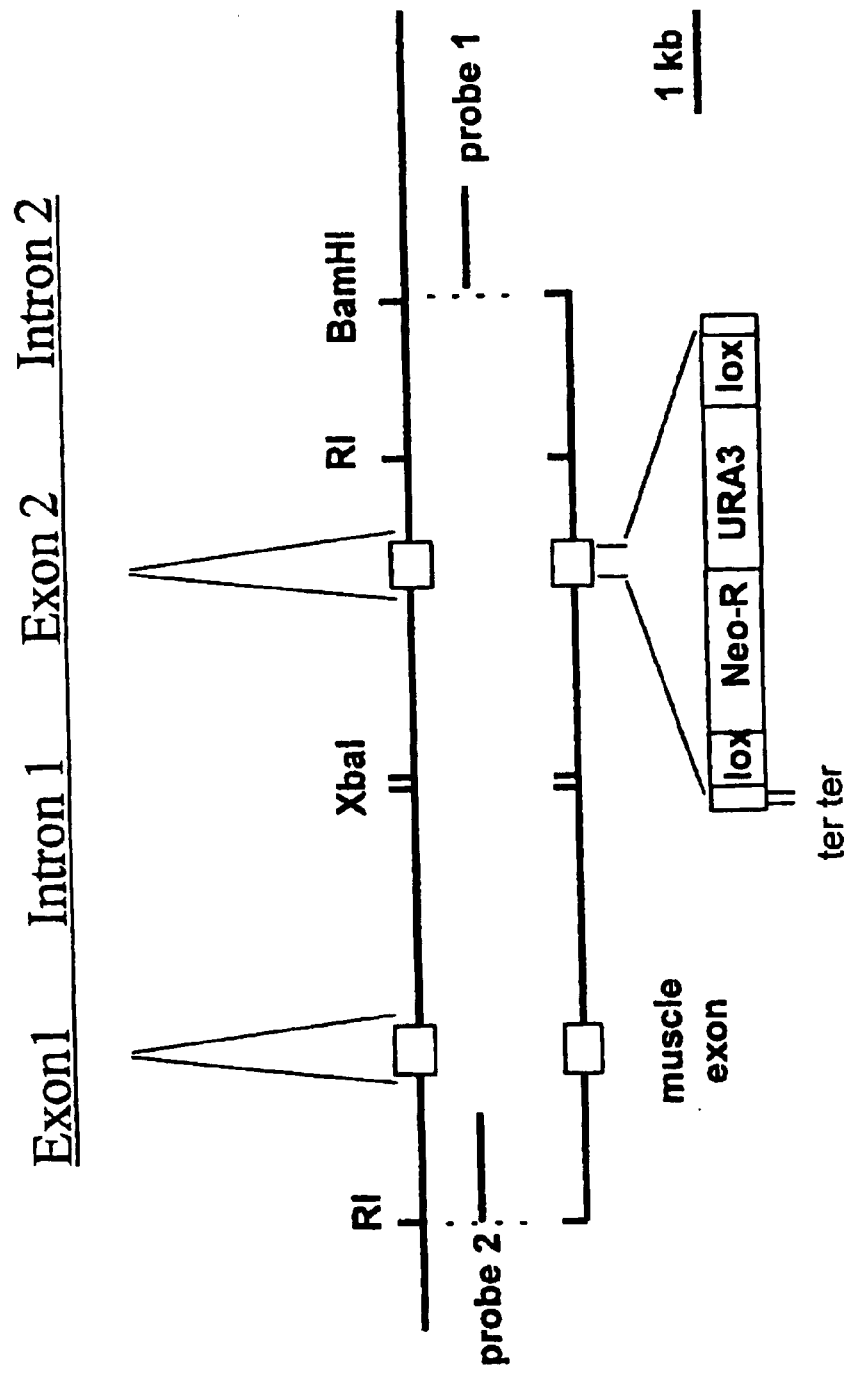
FIG. 1 illustrates the strategy for accomplishing targeted disruption of the PDE7A locus.

The present invention describes a method for developing a non-human transgenic animal that expresses either reduced, mutant, or no PDE7A gene products, or that expresses only human PDE7A gene products. Using this method, which is described below, it can now be demonstrated that a viable transgenic mouse, whose PDE7A gene has been inactivated, can be created.

Accordingly, the present invention provides a transgenic non-human animal in which a cAMP phosphodiesterase has been selectively inactivated. More specifically, the present invention provides a transgenic non-human animal whose genome comprises a disruption in the PDE7A gene, wherein the transgenic animal exhibits a decreased level of functional PDE7A protein relative to wild-type. The non-human animal may be any suitable animal (e.g., cat, cattle, dog, horse, goat, rodent, and sheep), but is preferably a rodent. More preferably, the non-human animal is a rat or a mouse.

Unless otherwise indicated, the term "PDE7A gene" refers herein to a nucleic acid sequence encoding PDE7A protein, and any allelic variants thereof. Due to the degeneracy of the genetic code, the PDE7A gene of the present invention includes a multitude of nucleic acid substitutions which will also encode PDE7A protein. An "endogenous" PDE7A gene is one that originates or arises naturally, from within an organism. Additionally, as used herein, "PDE7A protein" includes both a PDE7A protein and a "PDE7A analogue". A "PDE7A analogue" is a functional variant of the PDE7A protein, having PDE7A-protein biological activity, that has 60% or greater (preferably, 70% or greater) amino-acid-sequence homology with the PDE7A protein, as well as a fragment of the PDE7A protein having PDE7A-protein biological activity. As further used herein, the term "PDE7A-protein biological activity" refers to protein activity which regulates cAMP and modulates lymphocyte proliferation, as disclosed herein.

As used herein, the term "transgenic non-human animal" refers to a genetically-engineered non-human animal, produced by experimental manipulation, whose genome has been altered by introduction of a transgene. As further used herein, the term "transgene" refers to a nucleic acid (e.g., DNA or a gene) that has been introduced into the genome of an animal by experimental manipulation, wherein the introduced gene is not endogenous to the animal, or is a modified or mutated form of a gene that is endogenous to the animal. The modified or mutated form of an endogenous gene may be produced through human intervention (e.g., by introduction of a point mutation, introduction of a frameshift mutation, deletion of a portion or fragment of the endogenous gene, insertion of a selectable marker gene, insertion of a termination codon, etc.). A transgenic non-human animal may be produced by several methods involving human intervention, including, without limitation, introduction of a transgene into an embryonic stem cell, newly fertilized egg, or early embryo of a non-human animal; integration of a transgene into a chromosome of the somatic and/or germ cells of a non-human animal; and any of the methods described herein.

The transgenic animal of the present invention has a genome in which the PDE7A gene has been selectively inactivated, resulting in a disruption in its endogenous PDE7A gene. As used herein, a "disruption" refers to a mutation (i.e., a permanent, transmissable change in genetic material) in the PDE7A gene that prevents normal expression of functional PDE7A protein (e.g., it results in expression of a mutant PDE7A protein; it prevents expression of a normal amount of PDE7A protein; or it prevents expression of PDE7A protein). Examples of a disruption include, without limitation, a point mutation, introduction of a frameshift mutation, deletion of a portion or fragment of the endogenous gene, insertion of a selectable marker gene, and insertion of a termination codon. As used herein, the term "mutant" is used herein to refer to a gene (or its gene product) which exhibits at least one modification in its sequence (or its functional properties) as compared with the wild-type gene (or its gene product). In contrast, the term "wild-type" refers to the characteristic genotype (or phenotype) for a particular gene (or its gene product), as found most frequently in its natural source (e.g., in a natural population). A wild-type animal, for example, expresses functional PDE7A.

Selective inactivation in the transgenic non-human animal of the present invention may be achieved by a variety of methods, and may result in either a heterozygous disruption (wherein one PDE7A gene allele is disrupted, such that the resulting transgenic animal is heterozygous for the mutation) or a homozygous disruption (wherein both PDE7A gene alleles are disrupted, such that the resulting transgenic animal is homozygous for the mutation). In one embodiment of the present invention, the endogenous PDE7A gene of the transgenic animal is disrupted through homologous recombination with a nucleic acid sequence that encodes a region common to PDE7A gene products. By way of example, the disruption through homologous recombination may generate a knockout mutation in the PDE7A gene, particularly a knockout mutation wherein at least one deletion has been introduced into at least one exon of the PDE7A gene. In a preferred embodiment of the present invention, the knockout mutation is generated in a coding exon of the PDE7A gene. Preferably, the coding exon of the PDE7A gene is exon 2.

Additionally, in accordance with the methods of the present invention, a disruption in the PDE7A gene may result from insertion of a heterologous selectable marker gene into the endogenous PDE7A gene. As used herein, the term "selectable marker gene" refers to a gene encoding an enzyme that confers upon the cell or organism in which it is expressed a resistance to a drug or antibiotic, such that expression or activity of the marker can be selected for (e.g., a positive marker, such as the neo gene) or against (e.g., a negative marker, such as the dt gene). As further used herein, the term "heterologous selectable marker gene" refers to a selectable marker gene that, through experimental manipulation, has been inserted into the genome of an animal in which it would not normally be found. As the inventor has described herein, such a heterologous selectable marker gene may be inserted into any coding exon of the PDE7A gene. In a preferred embodiment, the coding exon of the PDE7A gene is exon 2.

The transgenic non-human animal of the present invention exhibits decreased expression of functional PDE7A protein relative to a corresponding wild-type non-human animal of the same species. As used herein, the phrase "exhibits decreased expression of functional PDE7A protein" refers to a transgenic animal in whom the detected amount of functional PDE7A is less than that which is detected in a corresponding animal of the same species whose genome contains a wild-type PDE7A gene. Preferably, the transgenic animal contains at least 50% less functional PDE7A than the corresponding wild-type animal. More preferably, the transgenic animal contains at least 75% less functional PDE7A than the corresponding wild-type animal. Even more preferably, the transgenic animal contains at least 90% less functional PDE7A than the corresponding wild-type animal. Levels of PDE7A in an animal, as well as PDE7A activity, may be detected using standard assays such as those known in the art.

Accordingly, where the transgenic animal of the present invention exhibits decreased expression of functional PDE7A protein relative to wild-type, the level of functional PDE7A protein in the transgenic animal is lower than that which otherwise would be found in nature. In one embodiment of the present invention, the transgenic animal expresses mutant PDE7A (regardless of amount). In another embodiment of the present invention, the transgenic animal expresses no PDE7A (wild-type or mutant). In yet another embodiment of the present invention, the transgenic animal expresses wild-type PDE7A protein, but at a decreased level of expression relative to a corresponding wild-type animal of the same species. As disclosed herein, the transgenic animal of the present invention retains the ability to express other cyclic nucleotide phosphodiesterases, mutant PDE7A proteins, and normal and mutant human PDE7A products.

The transgenic non-human animal of the present invention, or any transgenic non-human animal exhibiting decreased expression of functional PDE7A protein relative to wild-type, may be produced by a variety of techniques for genetically engineering transgenic animals. For example, to create a transgenic non-human animal exhibiting decreased expression of functional PDE7A protein relative to a corresponding wild-type animal of the same species, a PDE7A targeting vector first may be generated.

As used herein, the term "PDE7A targeting vector" refers to an oligonucleotide sequence that comprises a portion, or all, of the PDE7A gene, and is sufficient to permit homologous recombination of the targeting vector into at least one allele of the endogenous PDE7A gene within the recipient cell. In one embodiment of the present invention, the targeting vector further comprises a positive or negative heterologous selectable marker gene (e.g., the positive selection gene, neo). Additionally, the targeting vector may be a replacement vector (i.e., the selectable marker gene replaces an endogenous target gene). For example, the replacement vector of the present invention may insert a heterologous selectable marker gene into the PDE7A gene, resulting in a disruption of the PDE7A gene such that functional PDE7A protein is not expressed. Such a disruption is referred to herein as a "null" or "knockout" mutation. It is also within the scope of the present invention that the targeting vector may be an insertion vector. By way of example, the PDE7A targeting vector of the present invention may be an oligonucleotide sequence comprising at least a portion of a non-human PDE7A gene in which there is at least one deletion in at least one exon.

As described below, the inventor has devised a novel way to create an appropriate targeting vector for use in the creation of transgenic non-human animals such as those disclosed herein. In accordance with this novel method, a targeting vector for a particular gene is generated by introducing a termination codon and a heterologous selectable marker gene into a coding exon of the particular gene by homologous recombination in yeast. This method of generating a targeting vector is expected to be useful in creating any transgenic non-human animal whose genome contains a knockout mutation. For example, to create a transgenic non-human animal exhibiting decreased expression of functional PDE7A protein relative to wild-type, a PDE7A targeting vector may be generated by introducing a termination codon and a heterologous selectable marker gene into a coding exon of a PDE7A gene by homologous recombination in yeast. Thus, in one embodiment of the present invention, the PDE7A targeting vector is generated by introducing at least one termination codon and a heterologous selectable marker gene into a coding exon of a PDE7A gene by homologous recombination in yeast. In a preferred embodiment, the coding exon of the PDE7A gene is exon 2.

In the method of the present invention, the PDE7A targeting vector that has been generated then may be introduced into a recipient cell (comprising a wild-type PDE7A gene) of a non-human animal, to produce a treated recipient cell. This introduction may be performed under conditions suitable for homologous recombination of the vector into at least one of the wild-type PDE7A genes in the genome of the recipient cell. The non-human animal may be any suitable animal (e.g., cat, cattle, dog, horse, goat, rodent, and sheep), as described above, but is preferably a rodent. More preferably, the non-human animal is a rat or a mouse. The recipient cell may be, for example, an embryonic stem cell, or a cell of an oocyte or zygote.

The PDE7A targeting vector of the present invention may be introduced into the recipient cell by any in vivo or ex vivo means suitable for gene transfer, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, viral vectors, and naked DNA transfer, or any combination thereof. Recombinant viral vectors suitable for gene transfer include, but are not limited to, vectors derived from the genomes of viruses such as retrovirus, HSV, adenovirus, adeno-associated virus, Semiliki Forest virus, cytomegalovirus, and vaccinia virus.

In accordance with the methods of the present invention, the treated recipient cell then may be introduced into a blastocyst of a non-human animal of the same species (e.g., by injection or microinjection into the blastocoel cavity), to produce a treated blastocyst. Thereafter, the treated blastocyst may be introduced (e.g., by transplantation) into a pseudopregnant non-human animal of the same species, for expression and subsequent germline transmission to progeny. For example, the treated blastocyst may be allowed to develop to term, thereby permitting the pseudopregnant animal to deliver progeny comprising the homologously recombined vector, wherein the progeny may exhibit decreased expression of PDE7A relative to corresponding wild-type animals of the same species. It then may be possible to identify a transgenic non-human animal whose genome comprises a disruption in its endogenous PDE7A gene. The identified transgenic animal then may be interbred with other founder transgenic animals, to produce heterozygous or homozygous non-human animals exhibiting decreased expression of functional PDE7A protein relative to corresponding wild-type animals of the same species.

The present invention further provides a transgenic non-human animal created by the above-described method. The non-human animal may be any suitable animal (e.g., cat, cattle, dog, horse, goat, rodent, and sheep), as described above, but is preferably a rodent. More preferably, the non-human animal is a rat or a mouse.

Studies on the transgenic non-human animal of the present invention, which exhibits decreased expression of functional PDE7A protein relative to wild-type, and which lacks the wild-type PDE7A gene, may facilitate an understanding of the pathology of immunodeficiency diseases such as those described above. For example, the transgenic non-human animal could be used to test whether loss of PDE7A affects the development of certain acute and chronic inflammatory disorders believed to have an immunologic basis (e.g., arthritis, contact sensitivity, diabetes, and multiple sclerosis). The transgenic non-human animal also may be useful for screening immune responses to allergens, antigens, superantigens, and transplantations. Current model mice for these immune responses all express PDE7A.

Since PDE7A is currently being targeted for inhibition, studies using the transgenic non-human animal of the present invention also may provide an indication as to possible side-effects on organ systems, other than the immune system, that could arise when PDE7A is not functional. A transgenic non-human animal genetically engineered to express human PDE7A also will be a valuable reagent for testing lead PDE7A compounds in vivo.

Accordingly, the inventor's transgenic non-human animal could be used to determine whether inhibitors that have been developed to specifically target PDE7A have effects on other PDE isoforms, thereby producing physiological side-effects. Thus, the non-human transgenic animal of the present invention provides a valuable, unique, and useful reagent for screening for side-effects of PDE7A inhibitors, and candidate immunosuppressant and phosphodiesterase inhibitors that are not directed against PDE7A. In particular, the transgenic non-human animal of the present invention will be useful for screening candidate therapeutic agents in order to: (1) verify that the proper PDE has been targeted by the agent; (2) analyze the specificity of the candidate agent; (3) monitor for side-effects of the drugs; and (4) follow long-term effects of inhibition of PDE7A activity (e.g., compensatory effects, complications, etc.).

In view of the foregoing, the present invention further provides a method for screening a PDE7A inhibitor or enhancer for at least one side-effect (particularly deleterious side-effects) by administering a PDE7A inhibitor or enhancer to the transgenic non-human animal of the present invention, and detecting at least one side-effect, if any, of the PDE7A inhibitor or enhancer in the transgenic animal. PDE7A may be inhibited by disabling, disrupting, or inactivating the function or biological activity of PDE7A in a subject to whom a PDE7A inhibitor is administered, or by diminishing the amount of PDE7A in the subject. Furthermore, PDE7A may be inhibited by targeting PDE7A directly or indirectly.

As used herein, "a PDE7A inhibitor" shall include a protein, polypeptide, peptide, nucleic acid (including DNA, RNA, and an antisense oligonucleotide), antibody (monoclonal and polyclonal, as described above), Fab fragment (as described above), F(ab')$_2$ fragment (as described above), molecule, compound, antibiotic, drug, and any combinations thereof, and may be an agent reactive with PDE7A. As used herein, the term "reactive" means the agent has affinity for, binds to, or is directed against PDE7A.

Unless otherwise indicated, an "agent", as used herein, shall include a protein, polypeptide, peptide, ribonucleic acid (including RNA), deoxyribonucleic acid (including DNA), antisense RNA, antisense DNA, antibody, Fab fragment, F(ab')$_2$ fragment, molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion. The antibody of the present invention may be polyclonal or monoclonal, and may be produced by techniques well known to those skilled in the art. In one embodiment of the present invention, the PDE7A inhibitor inhibits proliferation of immune cells, including lymphocytes (e.g., T cells and B cells) and other lymphoid cells.

The specificity of PDE7A inhibitors and enhancers may be further studied in transgenic animals whose genomes lack endogenous PDE7A, but have been reconstituted with either human or rodent PDE7A forms (wild-type or mutant). If these inhibitors or enhancers are specific for PDE7A, reconstitution of PDE7A expression should confer sensitivity to the pharmacological effects of the PDE7A inhibitor and enhancer compounds.

The non-human transgenic animal of the present invention also may be useful as a standard control by which to identify and evaluate PDE7A inhibitors. Accordingly, the present invention further provides a method for screening an agent for ability to affect PDE7A activity, comprising the steps of: (a) providing a transgenic non-human animal exhibiting decreased expression of functional PDE7A protein relative to a corresponding wild-type animal of the same species; (b) providing a corresponding wild-type animal of the same species as the transgenic animal; (c) administering to the animals provided in steps (a) and (b) a stimulus that normally induces PDE7A to hydrolyze cAMP, and measuring cAMP levels in these animals following administration of the stimulus, wherein the level of cAMP in the animal provides a measurement of PDE7A activity in the animal; (d) administering to a subject the stimulus that normally induces PDE7A to hydrolyze cAMP, and thereafter measuring cAMP levels in the subject, wherein the subject may be any; (e) measuring the level of cAMP in the subject; and (f) comparing the measured cAMP level in the subject with measured cAMP level in the animals provided in steps (a) and (b), wherein the level of cAMP in the homozygous transgenic animal provides a standard of 0% PDE7A activity, the level of cAMP in the heterozygous transgenic animal provides a mid-level standard of PDE7A activity, and the level of cAMP in the subject, prior to administration of the PDE7A inhibitor, provides a standard of 100% PDE7A activity. Where an agent administered to a subject brings about a reduction in the level of cAMP in the subject, it may be concluded that the agent could be useful as a PDE7A inhibitor, as that term is described above.

Studies on the transgenic non-human animal of the present invention have, for the first time, firmly established a link between PDE7A and the proliferation and differentiation of immune cells, including lymphocytes (e.g., T cells and B cells) and other lymphoid cells. In particular, the inventor has confirmed, through in vivo methods described below, that PDE7A does play a role in the proliferation of immune cells. Therefore, inhibition of PDE7A may provide an appropriate therapy for treating immunologic responses and immunodeficiency conditions that are either caused by, or associated with, proliferation and/or accumulation of immune cells. Examples of such immunologic responses and immunodeficiency conditions include, without limitation, allergy; asthma; autoimmune disorders, such as Hashimoto's thyroiditis, systemic lupus erythematosus (SLE), Goodpasture's syndrome, Crohn's disease, pemphigus, receptor autoimmunity, Graves' disease, myasthenia gravis, insulin resistance, and autoimmune hemolytic anemia; chronic obstructive pulmonary disease (COPD); CLL; inflammation; and rheumatoid arthritis. Inhibition of PDE7A also may provide an appropriate therapy for treating acute and chronic inflammatory disorders believed to have an immunologic basis (e.g., arthritis, contact sensitivity, diabetes, and multiple sclerosis).

Accordingly, it is expected that PDE7A inhibitors will have pharmacological effects in wild-type animals, but not in animals lacking the PDE7A gene. Such compounds may have therapeutic applications in diseases or conditions associated with defects of the immune system (e.g., immunologic responses, immunodeficiency conditions, conditions associated with a proliferation of immune cells, and acute and chronic inflammatory disorders believed to have an immunologic basis), including all of those described above. In addition, they may be useful in other pathologies where regulation of PDE7A activity plays a role.

Therefore, the transgenic animal of the present invention represents a useful assay system for modulating immunologic and other physiological responses, and for screening candidate compounds for anti-proliferative or anti-differentiative effects on immune cells. Compounds with such anti-proliferative or anti-differentiative effects on immune cells may be useful for treating immunologic responses, immunodeficiency conditions, and inflammatory disorders believed to have an immunologic basis, including those described above, as well as hyperplasia associated with increased PDE7A expression. As used herein, "hyperplasia" refers to the abnormal multiplication or increase in the number of normal cells, in normal arrangement, within a tissue.

In view of the foregoing, it is within the confines of the present invention to provide a method for treating immunologic responses, immunodeficiency diseases, inflammatory disorders believed to have an immunologic basis, hyperplasias, and other conditions associated with proliferation of immune cells, in a subject in need of treatment, by inhibiting PDE7A in the subject, or by administering to the subject a PDE7A inhibitor. Examples of such conditions include, without limitation, allergy, asthma, autoimmune disorders, chronic lymphocytic leukemia (CLL), chronic obstructive pulmonary disease (COPD), contact sensitivity, diabetes, inflammation, multiple sclerosis, and rheumatoid arthritis.

It is also within the confines of the present invention that the transgenic non-human animals described herein may provide useful positive controls against which to evaluate the therapeutic efficacy of PDE7A inhibitors in treating immunologic responses, immunodeficiency diseases, inflammatory disorders believed to have an immunologic basis, hyperplasias, and other conditions associated with proliferation of immune cells. Accordingly, the present invention further provides a method for identifying an agent that is therapeutic for a condition associated with proliferation of immune cells by: (a) providing a transgenic non-human animal exhibiting decreased expression of PDE7A relative to a corresponding wild-type animal of the same species; (b) providing a non-human animal that has the condition associated with proliferation of immune cells; (c) providing a candidate agent believed to be capable of inhibiting PDE7A in an animal; (d) mating the transgenic non-human animal with the diseased animal to produce an offspring animal exhibiting decreased expression of PDE7A relative to the diseased animal; (e) detecting in the offspring animal a reduction in at least one symptom of the condition associated with proliferation of immune cells, thereby identifying a reduction in PDE7A activity as being therapeutic; (f) administering the candidate agent to the diseased animal, to produce a treated animal; and (g) detecting in the treated animal a reduction, relative to the diseased animal, in at least one symptom of the condition associated with proliferation of immune cells, thereby identifying the candidate agent as being therapeutic. Also provided herein is a candidate agent identified by this method of the present invention.

The non-human transgenic animal of the present invention also may be useful as a recipient of a normal human PDE7A gene, thereby providing a model system for screening human PDE7A inhibitors in vivo. It will be apparent to those of skill in the art that PDE7KO animals can be modified to contain and express DNA encoding a human PDE7A protein by any suitable technique. In such a case, the DNA encoding the human PDE7A protein is under the control of any suitable regulatory element for expressing the DNA.

The present invention is further described in the following Experimental Details section, which is set forth to aid in the understanding of the invention, and should not be construed to limit in any way the scope of the invention as defined in the claims which follow thereafter.

Experimental Details

1. Introduction

The present invention provides non-human transgenic animals in which a cAMP phosphodiesterase is selectively inactivated such that the transgenic animals express either reduced, mutant, or no PDE7A-encoded gene products, or express only the human PDE7A1, PDE7A2, or PDE7A3 proteins. Selective inactivation is achieved by the disruption, through homologous recombination, of a nucleic acid sequence which encodes a region common to all PDE7A-encoded proteins. In particular, the present invention describes transgenic animals which contain a disrupted PDE7A gene. These transgenic animals retain the ability to express other cyclic nucleotide phosphodiesterases, as well as normal and mutant human PDE7A-encoded proteins. The transgenic animals of the present invention may be used to screen candidate therapeutic compounds for antiproliferative effects, particularly on mammary and prostate hyperplasia, and for an ability to modulate immune and other physiological responses.

2. Materials and Methods

An 8.5-kb genomic DNA fragment containing the muscle-specific exon of PDE7A (referred to as exon 1), which is specific for PDE7A2, and the first exon common to all known PDE7A transcripts (referred to as exon 2), was cloned into the plasmid pRS314 between the EcoRI and the BamH1 sites. This plasmid was transformed into the yeast strain FY250 (Mata ura3-52 his3Δ200 leu2Δ1 trp1Δ3), and Trp+ colonies were selected. Several Trp+ colonies were transformed with a PCR fragment containing the NEO-R/URA3 marker genes flanked by oligonucleotide-derived sequences that were derived from PDE7A genomic sequences around the junctions of exon 2 and its flanking introns. Ura+Trp+ colonies that arose via homologous recombination then were selected. Plasmids were recovered from yeast, and the DNA sequence of the modified exon 2 was determined.

A. Generation of a PCR Fragment Containing PDE7A Sequences Flanking the NEO-R/URA3 Marker Genes Genomic sequences flanking exon 2 were determined, and then were used to design 5' and 3' oligonucleotides containing about 40 base pairs of PDE7A genomic sequence and about 24 base pairs derived from the plasmid pLox/NEO/URA3/Lox. PCR amplification of the pLox/NEO/URA3/Lox template with the 5' and the 3' oligonucleotides generated a 2.5-kb fragment with the sequence 5'-oligo-Lox/NEO/URA3/Lox-3'-oligo. This PCR fragment was used for homologous recombination into PDE7A genomic DNA cloned into pRS314.

An adenine residue within the 5' oligonucleotide generated an in-frame termination codon that can terminate translation from any transcripts arising from the promoter following the integration of the NEO/URA3 markers into the genome. Similarly, a termination codon downstream of the 3' oligonucleotide can terminate translation upon removal of Lox/NEO/URA3 sequences from the genome by the Cre recombinase (popout).

B. Embryonic Stem (ES) Cell Electroporation, Selection, and Microinjection into Mice Standard methods were used to generate Neo-resistant ES colonies containing the PDE7KO/NEO/URA3 sequences. Proper integration was determined by Southern blotting of XbaI-cut genomic DNA with probes at the 5' end of the 8.5-kb EcoRI-BamH1 PDE7A genomic fragment (1.4 kb) and flanking its 3' end (0.8 kb). 3 of the 65 colonies were positive. These were injected into blastocysts, and transplanted into pseudopregnant C57Bl6 females. Two independent colonies gave rise to four chimeric male mice. A cross into 129/SvJ females produced PDE7A-knockout (PDE7KO) heterozygous mice in a clean genetic background, while crosses into C57/Bl6 females initiated the backcrossing process. Crosses to ZP3-Cre mice are known to lead to the permanent excision of Lox/NEO/URA3 sequences from the genome of PDE7A-popout mice by the Cre recombinase in the gonads (1).

C. Genotyping of PDE7KO Mice

To amplify a 550 bp from WT DNA, the 5' oligonucleotide int1 5'-ttcccctc tcgttccctttga (SEQ ID NO:1) and the 3' oligonucleotide int2 5'-ctgagcgagcggagttgactg (SEQ ID NO:2) were used. To amplify a 450 bp from PDE7KO DNA, the 5' oligonucleotide URA3 5'-caaagggaagggatgctaaggta (SEQ ID NO:3) and the 3' oligonucleotide int2 5'-ctgagcgagcggagttgactg (SEQ ID NO:2) were used. To amplify a 614 bp from PDE7 popout DNA, the 5' oligonucleotide int1 5'-ttcccctctcgttccctttga (SEQ ID NO:1) and the 3' oligonucleotide int2 5'-ctgagcgagcggagttgactg (SEQ ID NO:2) were used.

3. Results

A. Generation of a Targeted Disruption of the PDE7A Gene, and the Resulting Phenotypes of PDE7A Knockout Mice (PDE7KO)

A PDE7A knockout construct was generated from genomic clones flanking exon 2—an exon shared by three splice variants, PDE7A1, PDE7A2, and PDE7A3. PDE7A genomic clones were supplied by Drs. C. Fletcher, N. Jenkins, and N. Copeland. A deletion within exon 2 was replaced by a PGK-NEO cassette flanked by a copy of a loxP site on either side (FIG. 1). The junction between the 5' loxP site and PDE7A exon 2 was mutated to include several in-frame termination codons that cause premature termination of any arising PDE7A-NEO transcripts. The knockout construct was generated via homologous recombination in yeast, and the resulting recombinant plasmid was sequenced. Subsequent to transfection to embryonic stem cells, clones with homologous recombination of the PDE7KO construct into the genome were identified by Southern blots using probes flanking the genomic fragment present in the PDE7KO construct.

3 out of 65 Neo-resistant clones were independent positive PDE7KO embryonic stem cell clones. These PDE7KO embryonic stem cell clones were injected into blastocysts, and chimeric mice from two independent PDE7KO lines were generated. Chimeric mice were crossed to C57/Bl6 females, and heterozygous progeny mice with germ-line transmission of the PDE7KO allele were genotyped by PCR analysis of tail clippings. These heterozygous F1 mice were crossed to each other to generate homozygous viable PDE7KO mice that did not exhibit obvious growth defects. These PDE7KO mice were in a mixed C57/Bl and 129/SvJ genetic background. PDE7KO mice then were backcrossed to C57Bl/6 background for 4 generations.

The PDE7KO phenotype demonstrated that compensatory expression/overexpression of other PDEs in the cells does not take place in the absence of endogenous PDE7A expression. Furthermore, it demonstrated that the PDEs present within cells have dedicated roles that cannot be easily provided by other PDEs within the cell. Differences in subcellular localization, in kinetic properties, and in the regulation of PDE activities distinguish the physiological roles of the PDEs and the cAMP pools which they control. For example, the PDE4DKO has fertility defects and defects in cholinergic airway responses, despite the presence of other PDEs in the ovary and lung (2).

B. Expression and Subcellular Localization of PDE7A2 in Skeletal Muscle of Wild-type and PDE7KO Mice To verify the knockout of PDE7A, the inventor examined the expression of the abundant muscle splice variant, PDE7A2. PDE7A2 expression was detected on Western blots of muscle extracts fractionated by low- and high-speed centrifugation (12,000 g and 150,000 g for the P1 and P2 fractions, respectively). A 50-kDa PDE7A2 protein band was apparent in muscle of wild-type mice, but not in tissues prepared from PDE7KO mice. Therefore, PDE7KO mice lack detectable expression of PDE7A2 proteins. In contrast, expression of caveolin-3 was not altered in PDE7KO muscles (data not shown).

Expression of the PDE7A1 splice variant in soluble fractions of fat, liver, pancreas, and pancreatic islets was examined by immunodetection on Western blots. PDE7A1 and 2 in wild-type and PDE7KO tissues was immunodetected with affinity-purified anti-PDE7A antibodies. Muscle extracts were fractionated to soluble (S, 100 μg), low-speed (P1, 25 μg), and high-speed (P2, 25 μg) fractions. PDE7A1 then was detected in soluble extracts of pancreas (pan, 100 μg), pancreatic islets (islet, 30 μg), fat (fat, 100 μg), and liver (liver, 100 μg). Low-level expression of PDE7A1 was observed in fat, pancreas, and pancreatic islets, but not in liver. PDE7A1 appears to be distributed evenly throughout the pancreas; enriched expression in the islets was not apparent. The inventor has hypothesized that PDE7A1 is primarily an exocrine pancreatic protein.

Immunolocalization of PDE7A2 in frozen sections of human fetal skeletal muscle was also detected using immunofluorescence and affinity-purified anti-PDE7 antibodies/Cy3-conjugated anti-rabbit secondary antibodies, and anti-caveolin 3 monoclonal antibodies/FITC-conjugated anti-mouse secondary antibodies were used. PDE7A2 of muscle was localized primarily to the P1 fraction, with plasma membrane and dense organelles, and to the P2 fraction, which contained low density organelles and vesicles. This localization is in agreement with the hydrophobic properties of the PDE7A2 N-terminus, and with results of immunofluorescence of a frozen section that localized PDE7A2 to the plasma membrane and to punctate, potentially vesicular cell structures of skeletal muscle. Thus, in skeletal muscle, PDE7A2 is localized to the site of cAMP synthesis, where it can effectively block the propagation of cAMP signals.

C. PDE7A RNA and Proteins

Expression of PDE7A1 and PDE7A2 mRNAs in PDE7KO mice was determined by RT-PCR analysis. PDE7KO mice expressed normal levels of PDE7A1, and reduced levels of PDE7A2 mRNA. The RT-PCR products of both PDE7A1 and PDE7A2 transcripts from PDE7KO mice were smaller than those of wild-type mice, when oligonucleotides located to the specific 5' ends of PDE7A1 and PDE7A2 were used in combination with an oligonucleotide common to their 3' ends. RT-PCR products amplified by oligonucleotides flanking exon 2 were smaller in PDE7KO mice than in wild-type mice, while those amplified with oligonucleotides located downstream to exon 2 were identical to those in wild-type mice. Thus, PDE7A transcripts of PDE7KO mice appear to lack exon 2 due to transcriptional skipping of exon 2. As anticipated, PDE7A mRNAs of popout mice contained an enlarged exon 2 (+64 bp).

Since skipping of exon 2 leads to in-frame deletion in PDE7A proteins, the protein product of PDE7A1 in PDE7KO mice was smaller than full-length PDE7A1. The abundance of PDE7A1 was reduced considerably in PDE7KO mice (10% of wild-type). Therefore, it appears that PDE7A protein products lacking exon 2 are unstable, even though their mRNA levels are not affected. Perhaps due to the proximity to exon 2 of the 5' end of the PDE7A2 transcript, both PDE7A2 mRNA and protein product were affected by exon 2 skipping. Consequently, PDE7A2 proteins are not detectable in PDE7KO mice.

The following oligonucleotides were used for RT-PCR analysis: PDE7A1 5'-ggcggacgtgttcaatggaagt (SEQ ID NO:4); PDE7A2 5'-ctgggagggctgttattcacc (SEQ ID NO:5); PDE7A 3'-ggcgactgatatccgtggctaat (SEQ ID NO:6); and PDE7A1 and A2 5'-gcgtgaggagccgagcag (SEQ ID NO:7).

D. Reduction of PDE Activities in PDE7KO Mice

Analysis of high-affinity cAMP PDE activities of skeletal muscle of PDE7KO mice demonstrated a 60% reduction in cAMP PDE activities of the P1 fraction to which the majority of PDE7A2 localized in muscle (Table I). Less significant reductions of ~16% in PDE activities of the soluble and the P2 fractions were noted, but their significance is not clear. In contrast, no reductions in cAMP PDE activities of fat cells of PDE7KO mice were observed. The contribution of rolipram-sensitive PDE4 to total PDE activities resulted in an increase only in muscle P1 fraction, suggesting that PDE4 activities did not compensate for the loss of PDE7A2 activity. Thus, the observed reductions in PDE activities of the muscle P1 fraction indicate that compensation for the loss of PDE7A2 via increases in PDE activities are either absent or undetectable in muscle; that PDE7A2 provides a non-redundant PDE activity in this tissue; and that the loss of PDE7A2 is likely to impact on cAMP signaling in muscle. Similar reductions were observed in PDE activities of soluble cerebral cortex extracts, demonstrating non-redundant contribution of PDE7A1 to PDE activities of this tissue.

TABLE I

Muscle/fat PDE activities (in pmoles/min/mg ± SD).

| Fat Cell Fraction | S | Skeletal Muscle | | |
|---|---|---|---|---|
| | | P1 | P2 | Total |
| Wild-type (n = 4) | 125.1 ± 28.7 | 58.3 ± 7.5 | 26.4 ± 1.5 | 145.75 ± 19.25 |
| % PDE4 (rolipram$^S$) | 81.2 | 45 | 66.8 | 33 |
| PDE7KO (n = 4) | 104.3 ± 8.7[1] | 24 ± 3.3[2] | 22.2 ± 2.3[3] | 149.9 ± 8.25[4] |
| % PDE4 (rolipram$^S$) | 82.8 | 85 | 56 | 28 |

Significance in comparison to wild-type: [1]<0.05; [2]<0.006; [3]<0.003; [4]<0.05

E. Effects of PDE7KO on Growth and Development

PDE7KO mice were viable, and did not exhibit any growth, behavioral, or life-span defects.

F. Effects of PDE7KO on Proliferation of Splenocytes and Purified T Cells

Cultured splenocytes proliferate in response to antibody activation of the T cell receptor (anti-CD3 antibodies). However, only limited proliferation of PDE7KO splenocytes in response to CD3 stimulation is feasible. In response to stimulation with 2 μg/ml anti-CD3 antibodies, 2×10$^5$ wild-type splenocytes incorporated 3.2×10$^4$ (±0.6×10$^4$) cpm of $^3$H-thymidine into their DNA, while PDE7KO splenocytes incorporated only 1.1×10$^4$ (±0.4×10$^4$) cpm of $^3$H-thymidine (36%) into their DNA during a 24-hour labelling period (P<0.02). In contrast, no difference was apparent between proliferation of wild-type and PDE7KO splenocytes in response to 5 ng/ml PMA and 100 ng/ml ionomycin: 2×10$^4$ and 1.8×0$^4$ cpm of $^3$H-thymidine, respectively. Thus, T cells of PDE7KO mice proliferate normally in response to direct activation of PKC and elevated intracellular calcium concentrations, but not in response to extracellular stimulation of T cell receptors.

The ability of purified T cells of PDE7KO mice to proliferate in response to CD3 stimulation was limited when compared to wild-type mice. T cells were purified by depletion of B cells, macrophages, and natural killer cells from splenocytes via use of antibodies attached to magnetic beads. Splenocytes purified in this manner were composed of >96% T cells. In response to stimulation with 2 μg/ml anti-CD3 antibodies, $2\times10^5$ wild-type splenocytes incorporated $1\times10^4$ ($\pm0.1\times10^4$) cpm of $^3$H-thymidine into their DNA, while PDE7KO splenocytes incorporated only $0.4\times10^4$ ($\pm0.01\times10^4$) cpm of $^3$H-thymidine (40%) into their DNA during a 24-hour labelling period. Thus, PDE7A is required for T cells to efficiently proliferate upon stimulation of the T cell receptor.

Production of interferon γ (INFγ) was impaired in PDE7KO mice. While 15% of wild-type CD4 cells produced detectable levels of intracellular INFγ upon T cell receptor activation with anti-CD3 antibodies, in only 10% of PDE7KO CD4 cells was intracellular INFγ detectable. Similarly, secretion of INFγ into the medium from PDE7KO splenocytes, in response to T cell receptor activation, was limited: 6 ng/ml vs. 10 ng/ml for PDE7KO and wild-type, respectively. Similar results were obtained with purified T cells, where 4.3% of wild-type CD4 cells, and 1.5% of PDE7KO CD4 cells, produced detectable levels of intracellular INFγ upon T cell receptor activation with anti-CD3 antibodies. T cells purified from wild-type and PDE7KO splenocytes secreted 1.5 and 1.2 ng/ml, respectively, of INFγ into the medium. Thus, in response to activation of the T cell receptor, PDE7KO T cells are defective in proliferation and in cytokine production and secretion.

G. In Vivo T Cell Proliferation in Response to Stimulation of the T Cell Receptor with Antibodies T cell proliferation and INFγ production by PDE7KO T cells were impaired in vivo. Following injection of 10 μg anti-CD3 antibodies into mice for 8 h, examination of T cell proliferation in culture demonstrated that $2\times10^5$ wild-type splenocytes incorporated $2.2\times10^4$ ($\pm0.5\times10^4$) cpm of $^3$H-thymidine into their DNA, while PDE7KO splenocytes incorporated only $1.6\times10^4$ ($\pm0.5\times10^4$) cpm of $^3$H-thymidine upon T cell receptor activation. With p<0.04, it appears that in vivo T cell proliferation is limited in the absence of PDE7A (70%). Furthermore, production of INFγ in CD4 cells and CD8 cells of PDE7KO mice was attenuated. While 1.2% of wild-type CD4 cells, and 2.6% of wild-type CD8 cells, stained positive for INFγ production, only 0.6% of PDE7KO CD4 cells, and 1.5% of PDE7KO CD8 cells, produced detectable levels of intracellular INFγ upon T cell receptor activation with anti-CD3 antibodies.

H. Expression Pattern of PDE7A1

Immunodetection of PDE7A1 proteins in several tissues demonstrated that PDE7A1 was abundant in the cerebral cortex, cerebellum, thymus, spleen, lung, and kidney, and nearly absent from fat and liver. Notably, PDE7A1 was present in purified B cells, and its expression was drastically stimulated upon B cell activation with LPS. Furthermore, the expression of PDE7A1 was markedly increased in breast tumors in transgenic animals expressing an activated-neu allele in the breast tissue.

I. Significance of Immunological Observations

The viability of PDE7KO and popout mice suggests that anti-PDE7 therapy is not likely to cause strong human developmental or physiological effects. Additionally, limited proliferation of T cells derived from PDE7KO mice in response to T cell receptor activation in culture and in vivo suggests that anti-PDE7 therapy can be used to treat conditions involving detrimental T cell proliferation, including allergic and rheumatic responses, autoimmune diseases, transplantation, and others. Finally, PDE7A is a potential therapeutic target for conditions involving unwanted B cell proliferation.

J. Blood Glucose Levels of PDE7KO Mice

Measurements of blood glucose levels of PDE7KO mice were taken in the fed state, at midnight, with a glucometer (Glucometer Elite, Bayer). Analysis of 15 PDE7KO mice and 10 wild-type littermates, ranging in age from 2 months to >7 months, on several occasions, established the average fed glucose levels detailed in Table II. PDE7KO mice exhibited moderate elevations in their blood glucose levels in comparison to wild-type mice. Significant elevation of fed glucose levels in PDE7KO mice was observed only in young mice (<5 months old). Thus, these measurements show that PDE7KO mice are not hyperglycemic.

TABLE II

Average fed glucose levels.

| | Fed glucose levels (in mg/dL ± SD) | | | Fed insulin levels (in ng/ml ± SE) | |
|---|---|---|---|---|---|
| | 2–4 months | 5–6 months | >7 months | 5–6 months | >7 months |
| Wild-type (n = 10) | 126.6 ± 22.1 | 135.6 ± 20.6 | 142.8 ± 20.9 | 5.4 ± 1 | 3.2 ± 0.3 |
| PDE7KO (n = 15) | 161 ± 33.5 | 158.5 ± 25.3 | 155.6 ± 24.5 | 5.9 ± 2 | 3.8 ± 0.5 |
| Significance | <0.05 | — | — | — | — |

K. Glucose Tolerance of PDE7KO Mice

PDE7KO mice were analyzed for their ability to clear an intraperitoneal glucose injection. Wild-type and PDE7KO mice were starved overnight, and were subsequently injected intraperitoneally with 2 mg glucose per gram body weight. Blood glucose levels were measured before the injection, and at 15, 30, 60 and 90 min after the injection with a glucometer. Analysis of 15 PDE7KO mice and 10 wild-type littermates, on multiple occasions, demonstrated that PDE7KO mice did not clear glucose within 90 min of injection, and that their glucose levels were significantly higher than those of their wild-type littermates. Only after 150 min did glucose levels of PDE7KO mice drop to 200 mg/dL (data not shown). As fasted glucose levels were not different in wild-type and PDE7KO mice, it appears that PDE7KO mice clear glucose slowly, and that an overnight fast can restore basal blood glucose levels. Thus, these measurements demonstrate that PDE7KO mice are glucose intolerant.

L. Insulin Resistance in PDE7KO Mice

The ability of PDB7KO mice to clear glucose in the presence of injected insulin serves as a measure for overall insulin resistance of the animal. To assess insulin resistance of PDE7KO mice, the mice were injected intraperitoneally with 1U insulin/kg body weight, and blood glucose levels were determined 30 and 60 min later (Table III). While young mice were not resistant to insulin, PDE7KO mice >7 months of age were significantly more resistant to insulin than were wild-type littermates. These observations demonstrate age-dependent deterioration in glucose homeostasis in PDE7KO mice, and are consistent with the hypothesis that defects in muscle glucose uptake underlie perturbations of glucose homeostasis in PDE7KO mice.

TABLE III

Determination of blood glucose levels.

| | Glucose Clearance | | | |
|---|---|---|---|---|
| | Mice 4–6 months; n = 4 % glucose cleared after insulin injection | | Mice >7 months; n = 8 % glucose cleared after insulin injection | |
| | 30' | 60' | 30' | 60' |
| WT | 51.5 ± 12 | 69 ± 12.8 | 58.4 ± 10 | 61.7 ± 13.8 |
| PDE7KO | 53.2 ± 15.5 | 59.5 ± 12.8 | 81.3 ± 15.1 | 82.6 ± 12.3 |
| Significance | — | — | <0.01 | <0.03 |

M. Circulating Free Fatty Acids (FFAs) in PDE7KO Mice

Increased circulating FFA levels contribute to perturbations of glucose homeostasis in metabolic syndrome X and NIDDM. Circulating FFAs were measured in serum samples that were kept on ice at all times. The samples were analyzed immediately after they were drawn from fasted animals and the blood cells were removed using NEFA-kit-U (Amano Enzyme). FFA determinations in young PDE7KO mice demonstrated that, in the fasted state, young PDE7KO mice exhibited a 30% increase in circulating FFAs (Table IV). However, FFA levels of PDE7KO mice >7 months of age were not different from those of wild-type littermates. The observed elevation in FFA levels of young PDE7KO mice suggests that enhanced lipolysis occurs at the age of 2–4 months. Increased lipolysis, however, is transient, and is not evident in older PDE7KO mice. Thus, it appears that enhanced lipolysis accompanies, but is not essential for, the manifestation of glucose intolerance and/or insulin resistance in PDE7KO mice. Measurements of fat pads weight upon animal sacrifice and microscopic examination of adipocytes morphology.

TABLE IV

Analysis of circulating FFAs.

| | Free fatty acids (in mEq/dL ± SD) | | Fat pads |
|---|---|---|---|
| | 2–4 months | >7 months | gr ± SD |
| Wild-type | 861 ± 242 | 993 ± 295 | 6.58 ± 0.55 |
| n | 6 | 10 | 4 |
| PDE7KO | 1120 ± 271 | 1062 ± 412 | 6.85 ± 0.51 |
| n | 8 | 15 | 4 |
| Significance | <0.07 | — | — |

N. Circulating Insulin Levels and Insulin Secretion in PDE7KO Mice

Blood insulin levels in the fed state were examined to determine whether compensatory increases in insulin secretion accompany the glucose intolerance of PDE7KO mice. Fed insulin levels were determined on multiple occasions by RIAs. Insulin levels in the fed state, in both wild-type and PDE7KO mice, were comparable (see Table II above). Despite a notable statistical variation, these measurements indicate that PDE7KO mice, of all ages, are not hyperinsulinemic.

To obtain a more accurate estimate of insulin secretion in PDE7KO mice, the inventor measured insulin levels upon injection of known quantities of glucose into fasted animals (Table V). A similar three-fold induction of insulin levels was observed upon intraperitoneal injection of glucose into fasted mice. Though statistical variation was notable, these measurements demonstrated no significant differences between insulin levels of PDE7KO and wild-type mice in response to glucose.

TABLE V

Analysis of insulin secretion in PDE7KO mice.

| | Insulin levels | | | |
|---|---|---|---|---|
| | Insulin ng/ml ± SD | | | |
| | | Glucose | % insulin secreted from islets ± SD | |
| | Starvation | injection | 1.67 mM glucose | 16.7 mM glucose |
| WT | 0.6 ± 0.36 | 1.84 ± 1.2 | 1.04 ± 1 | 4.3 ± 2.1 |
| PDE7KO | 0.6 ± 0.39 | 1.85 ± 1.1 | 0.78 ± 0.03 | 5.2 ± 2.4 |
| n | 4 | 4 | 6 | 6 |

Since low-level expression of PDE7A is evident in the pancreas and the pancreatic islets, the inventor examined glucose-induced insulin secretion from isolated islets in order to determine if elevations in intracellular cAMP levels resulting from ablation of PDE7A in β-cells are sufficient to facilitate glucose-induced insulin secretion in the absence of the nutritional, hormonal, and neural regulation to which islets are subjected in the complex animal environment. Islets were incubated in Hepes-buffered Krebs-Ringer solution containing 1.67 mM glucose, for 1 h, and subsequently stimulated with 16.7 mM glucose for 2 h. Following islet preparation, insulin was measured. No significant elevations in insulin secretion were observed in PDE7KO islets. The small increase in insulin secretion in PDE7KO islets was not statistically significant, and no significant differences were observed at intermediate glucose concentrations of 5 and 10 mM (data not shown). These observations demonstrate that insulin secretion from islets isolated from PDE7KO mice is not enhanced. Measurements of pancreatic and islet weights did not vary significantly between PDE7KO and wild-type littermates (data not shown). Histological examination of stained pancreatic sections did not reveal differences in islet prevalence and morphology.

In summary, measurements of circulating insulin in the fed state, in starved and stimulated mice, and in isolated islets, indicate that PDE7KO mice are not hyperinsulinemic, that they respond similarly to intraperitoneal glucose injection, and that their pancreatic islets, when isolated, are not limited in their ability to respond to glucose. Since islet mass is not drastically altered in PDE7KO mice, and since PDE7KO mice do not develop hyperglycemia and overt diabetes, a strong contribution of pancreatic β-cells to the PDE7KO phenotypes is not likely.

O. 2-deoxyglucose Uptake in Skeletal Muscle of PDE7KO Mice

To determine whether PDE7KO mice have defects in muscle glucose uptake, the inventor sought to examine the insulin-stimulated uptake of $^{14}$C-2-deoxyglucose (2DOG) into muscles and fat in older PDE7KO mice. For this purpose, the inventor analyzed 2DOG uptake in starved mice that were first injected intraperitoneally with insulin, and then, 15 min later, injected with $^{14}$C-2DOG via a tail vein. These are conditions of low glycemia and hyperinsulinemia, and are a mimic of clamp studies. Blood samples for glucose and $^{14}$C-2DOG content were taken at time 0 and 5–10 min thereafter.

Thirty minutes after $^{14}$C-2DOG injection, mice were killed, and their tissues were removed and analyzed for content of $^{14}$C-2DOG and $^{14}$C-2DOG-6P (Table VI). Based on analysis of blood glycemia and $^{14}$C-2DOG clearance, as well as tissue content of $^{14}$C-2DOG-6P, it appears that glucose uptake in the soleus and gastrocenimus muscles was inhibited by 45% and 50%, respectively. Glucose uptake in fat was not affected. These observations strongly support the hypothesis that defects in muscle glucose uptake underlie perturbations in glucose homeostasis in PDE7KO mice.

TABLE VI

Analysis of $^{14}$C-2DOG and $^{14}$C-2DOG-6P content.

| | $^{14}$C-2DOG uptake (ng/mg/min ± SD) | | | |
|---|---|---|---|---|
| | WT | PDE7KO | n | P |
| Soleus | 24.95 ± 3.1 | 13.8 ± 0.11 | 4 | <0.05 |
| Gastrocen. | 16.9 ± 2.7 | 8.2 ± 0.3 | 4 | <0.05 |
| Fat (white) | 3 ± 0.8 | 4 ± 0.9 | 4 | — |

P. Summary

Mice lacking PDE7A proteins and activities are viable, and do not exhibit gross morphological or behavioral defects. Reductions in cAMP PDE activities of PDE7KO mice indicate a unique and non-redundant role for PDE7A in muscle cAMP signaling and physiology. PDE7KO mice exhibit glucose intolerance and insulin resistance. However, PDE7KO mice are neither hyperinsulinemic nor hyperglycemic, and their pancreatic islets are neither sensitized nor resistant to glucose. Glucose uptake of PDE7KO by skeletal muscle is impaired, while adipose tissue is not affected. These observations strongly support the hypothesis that PDE7KO mice have a primary defect in insulin-stimulated glucose uptake in skeletal muscle that may not be fully compensated for by increased insulin secretion.

4. Discussion

The inventor has described herein the development of a viable PDE7A knock-out mouse with severe immune defects. The inventor's studies on this mouse have shown that PDE7A is not an essential gene, although it does have an important role in regulating proliferation of immune cells. A role for PDE7 in T cell activation in culture previously has been hypothesized by Li et al. (3), who used antisense oligonucleotides to PDE7 in human T cells.

Because the transgenic mouse of the present invention is viable, it may provide valuable information about possible side-effects that result from the inhibition of PDE7A, and facilitate an understanding of the pathology of immune disease. For example, the mouse could be used to test whether loss of PDE7A affects the development of certain acute and chronic inflammatory disorders believed to have an immunological basis (e.g., arthritis, contact sensitivity, diabetes, and multiple sclerosis).

Since PDE7A is currently being targeted for inhibition, studies using the transgenic mouse of the present invention also may provide an indication as to possible effects on organ systems, other than the immune system, that could arise when PDE7A is not functional. A transgenic mouse expressing human PDE7A also will be a valuable reagent for testing lead PDE7A compounds in vivo.

Additionally, the inventor's PDE7KO mouse could be used to determine whether inhibitors that have been developed to specifically target PDE7A have effects on other PDE isoforms, thereby producing physiological side-effects. In particular, the transgenic mouse of the present invention will be useful for screening candidate therapeutic agents in order to: (1) verify that the proper PDE has been targeted by the agent; (2) to monitor for side-effects of the drugs; and (3) to follow long-term effects of inhibition of PDE7A activity (e.g., compensatory effects, complications, etc.). The mouse also will be useful for screening immune responses to allergens, antigens, superantigens, and transplantations. Current model mice for these immune responses all express PDE7A. Finally, the inventor's PDE7KO mouse could be useful for screening for insulin-sensitizing drugs.

REFERENCES

1. Lewandoski et al., *Curr. Biol.*, 7:148–51, 1997.
2. Hansen et al., *PNAS*, 97(12):6751–56, 2000.
3. Li et al., *Science*, 283:848–51, 1999.

Cloning of PDE7:

4. Michaeli et al., Isolation and characterization of a previously undetected human cAMP phosphodiesterase by complementation of cAMP phosphodiesterase-deficient *Saccharomyces cerevisiae*. *Journal of Biological Chemistry*, 268:12925–32, 1993.
5. Bloom and Beavo, Identification and tissue-specific expression of PDE7 phosophodiesterase splice variants. *Proceedings of the National Academy of Sciences of the United States of America*, 93:14188–92, 1996.
6. Han et al., Alternative splicing of the high affinity cAMP-specific phosphodiesterase (PDE7A) mRNA in human skeletal muscle and heart. *Journal of Biological Chemistry*, 272:16152–57, 1997.

Presence of PDE7, or PDE7-like Activities, in T Cells:

7. Ichimura and Kase, A new cyclic nucleotide phosphodiesterase isozyme expressed in the T-lymphocyte cell lines. *Biochemical & Biophysical Research Communications*, 193:985–90, 1993.
8. Giembycz et al. Identification of cyclic AMP phosphodiesterases 3, 4 and 7 in human CD4+ and CD8+ t-lymphocytes: role in regulating proliferation and the biosynthesis of interleukin-2. *J. Pharmocology*, 118:1945–58, 1996.
9. Bloom and Beavo, Identification and tissue-specific expression of PDE7 phosophodiesterase splice variants. *Proc Natl Acad Sci U S A*, 93:14188–92, 1996.
10. Li et al., CD3- and CD28-dependent induction of PDE7 required for T cell activation. *Science*, 283:848–51, 1999.
11. Glavas et al., T cell activation up-regulates cyclic nucleotide phosphodiesterases 8A1 and 7A3. *Proc Natl Acad Sci U S A*, 98:6319–24, 2001.

Effects of cAMP on T/B Cell Proliferation:

12. Giembycz et al., Identification of cyclic AMP phosphodiesterases 3, 4 and 7 in human CD4+ and CD8+ t-lymphocytes: role in regulating proliferation and the biosynthesis of interleukin-2. *J. Pharmocology*, 118:1945–58, 1996.
13. Essayan, Cyclic nucleotide phosphodiesterase (PDE) inhibitors and immunomodulation. *Biochem. Pharmacol.*, 57:965–73, 1999.
14. Essayan et al., Modulation of antigen- and mitogen-induced proliferative responses of peripheral blood mononuclear cells by nonselective and isozyme selective cyclic nucleotide phosphodiesterase inhibitors. *J. Immunol.*, 153:3408–16, 1994.
15. Braun et al., Co-regulation of antigen-specific T lymphocyte responses by type I and type II cyclic AMP-dependent protein kinases (cAK). *Biochem. Pharmacol.*, 56:871–79, 1998.

16. Essayan et al. Differential efficacy of lymphocyte- and monocyte-selective pretreatment with a type 4 phosphodiesterase inhibitor on antigen-driven proliferation and cytokine gene expression. *J. Allergy Clin. Immunol.*, 99:28–37, 1997.
17. Lerner A, et al. The cAMP signaling pathway as a therapeutic target in lymphoid malignancies. *Leuk. Lymphoma*, 37:39–51, 2000.

General Immunology References:

18. Michaeli et al., Isolation and characterization of a previously undetected human cAMP phosphodiesterase by complementation of cAMP phosphodiesterase-deficient *Saccharomyces cerevisiae*. *Journal of Biological Chemistry*, 268:12925–32, 1993.
19. Bloom and Beavo, Identification and tissue-specific expression of PDE7 phosophodiesterase splice variants. *Proc Natl Acad Sci U S A*, 93, 14188–92, 1996.
20. Han et al., Alternative splicing of the high affinity cAMP-specific phosphodiesterase (PDE7A) mRNA in human skeletal muscle and heart. *Journal of Biological Chemistry*, 272:16152–57, 1997.
21. Ichimura and Kase, A new cyclic nucleotide phosphodiesterase isozyme expressed in the T-lymphocyte cell lines. *Biochemical & Biophysical Research Communications*, 193:985–90, 1993.
22. Giembycz et al., Identification of cyclic AMP phosphodiesterases 3, 4 and 7 in human CD4+ and CD8+ t-lymphocytes: role in regulating proliferation and the biosynthesis of interleukin-2. *J. Pharmocology*, 118:1945–58, 1996.
23. Li et al., CD3- and CD28-dependent induction of PDE7 required for T cell activation. *Science*, 283:848–51, 1999.
24. Glavas et al., T cell activation up-regulates cyclic nucleotide phosphodiesterases 8A1 and 7A3. *Proc Natl Acad Sci U S A*, 98:6319–24, 2001.
25. Essayan, Cyclic nucleotide phosphodiesterase (PDE) inhibitors and immunomodulation. *Biochem. Pharmacol.*, 57:965–73, 1999.
26. Essayan et al., Modulation of antigen- and mitogen-induced proliferative responses of peripheral blood mononuclear cells by nonselective and isozyme selective cyclic nucleotide phosphodiesterase inhibitors. *J. Immunol.*, 153:3408–16, 1994.
27. Braun et al., Co-regulation of antigen-specific T lymphocyte responses by type I and type II cyclic AMP-dependent protein kinases (cAK). *Biochem. Pharmacol.*, 56:871–79, 1998.
28. Essayan et al., Differential efficacy of lymphocyte- and monocyte-selective pretreatment with a type 4 phosphodiesterase inhibitor on antigen-driven proliferation and cytokine gene expression. *J. Allergy Clin. Immunol.*, 99:28–37, 1997.
29. Lerner et al., The cAMP signaling pathway as a therapeutic target in lymphoid malignancies. *Leuk. Lymphoma*, 37:39–51, 2000.
30. Essayan et al., Differential regulation of human antigen-specific Th1 and Th2 lymphocyte responses by isozyme selective cyclic nucleotide phosphodiesterase inhibitors. *J. Pharmacol. Exp. Ther.*, 282, 505–12, 1997.
31. Han et al., Assignment of the mouse Pde7A gene to the proximal region of chromosome 3 and of the human PDE7A gene to chromosome 8q13. *Genomics*, 48:275–76, 1998.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A transgenic mouse whose genome comprises a homozygous disruption in its endogenous PDE7A gene, wherein the transgenic mouse does not exhibit expression of functional PDE7A protein and wherein the transgenic mouse exhibits one or more of an immune defect, glucose intolerance, or insulin resistance relative to wild-type.

2. The transgenic mouse of claim 1, wherein the disruption comprises at least one deletion in at least one exon of the PDE7A gene.

3. The transgenic mouse of claim 1, wherein the disruption comprises insertion of a heterologous selectable marker gene into the endogenous PDE7A gene.

4. The transgenic mouse of claim 3, wherein the heterologous selectable marker gene is inserted into a coding exon of the endogenous PDE7A gene.

5. The transgenic mouse of claim 4, wherein the coding exon of the endogenous PDE7A gene is exon 2.

6. A method for creating a transgenic mouse whose genome comprises a homozygous disruption in its endogenous PDE7A gene, wherein the transgenic mouse does not exhibit expression of functional PDE7A protein and wherein the transgenic mouse exhibits one or more of an immune defect, glucose intolerance, or insulin resistance relative to wild-type, comprising the steps of:

(a) generating a PDE7A targeting vector;
(b) introducing the PDE7A targeting vector into a recipient embryonic stem cell of a mouse, to produce a treated recipient embryonic stem cell;
(c) introducing the treated recipient embryonic stem cell into a blastocyst of a mouse, to produce a treated blastocyst;
(d) introducing the treated blastocyst into a pseudopregnant mouse;
(e) allowing the transplanted blastocyst to develop to term to obtain a chimeric mouse;
(f) breeding the chimeric mouse of step (e) to obtain a heterozygous transgenic mouse: and
(g) breeding the heterozygous transgenic mouse of step (f) to obtain a homozygous transgenic mouse whose genome comprises a disruption in its endogenous PDE7A gene.

7. The method of claim 6, wherein the PDE7A targeting vector is generated by introducing at least one termination codon and a heterologous selectable marker gene into a coding exon of a PDE7A gene by homologous recombination in yeast.

8. The method of claim 7, wherein the coding exon of the PDE7A gene is exon 2.

9. The transgenic mouse of claim 1, wherein the transgenic mouse exhibits an immune defect relative to wild-type.

10. The transgenic mouse of claim 1, wherein the transgenic mouse exhibits glucose intolerance relative to wild-type.

11. The transgenic mouse of claim 1, wherein the transgenic mouse exhibits insulin resistance relative to wild-type.

12. The method of claim 6, wherein the transgenic mouse exhibits an immune defect relative to wild-type.

13. The method of claim 6, wherein the transgenic mouse exhibits glucose intolerance relative to wild-type.

14. The method of claim 6, wherein the tansgenic mouse exhibits insulin resistance relative to wild-type.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: 5' oligonucleotide int1, used to amplify
      wild-type PDE7A DNA

<400> SEQUENCE: 1
ttcccctctc gttccctttg a                                              21

<210> SEQ ID NO 2
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: 3' oligonucleotide int2, used to amplify
      wild-type PDE7A DNA

<400> SEQUENCE: 2
```

-continued

```
ctgagcgagc ggagttgact g                                                 21
```

<210> SEQ ID NO 3
<211> LENGTH: 23
<212> TYPE: DNA
<213> ORGANISM: Artificial Sequence
<220> FEATURE:
<221> NAME/KEY: primer_bind
<222> LOCATION: (1)..(23)
<223> OTHER INFORMATION: 5' oligonucleotide URA3, used to amplify
      PDE7KO DNA

<400> SEQUENCE: 3

```
caaagggaag ggatgctaag gta                                               23
```

<210> SEQ ID NO 4
<211> LENGTH: 22
<212> TYPE: DNA
<213> ORGANISM: Artificial Sequence
<220> FEATURE:
<221> NAME/KEY: primer_bind
<222> LOCATION: (1)..(22)
<223> OTHER INFORMATION: 5' oligonucleotide PDE7A1, used for RT-PCR
      analysis

<400> SEQUENCE: 4

```
ggcggacgtg ttcaatggaa gt                                                22
```

<210> SEQ ID NO 5
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: 5' oligonucleotide PDE7A2, used for RT-PCR
      analysis

<400> SEQUENCE: 5

```
ctgggagggc tgttattcac c                                                 21
```

<210> SEQ ID NO 6
<211> LENGTH: 23
<212> TYPE: DNA
<213> ORGANISM: Artificial Sequence
<220> FEATURE:
<221> NAME/KEY: primer_bind
<222> LOCATION: (1)..(23)
<223> OTHER INFORMATION: 3' oligonucleotide PDE7A, used for RT-PCR
      analysis

<400> SEQUENCE: 6

```
ggcgactgat atccgtggct aat                                               23
```

<210> SEQ ID NO 7
<211> LENGTH: 18
<212> TYPE: DNA
<213> ORGANISM: Artificial Sequence
<220> FEATURE:
<221> NAME/KEY: primer_bind
<222> LOCATION: (1)..(18)
<223> OTHER INFORMATION: 3' oligonucleotide PDE7A1/A2, used for RT-PCR
      analysis

<400> SEQUENCE: 7

```
gcgtgaggag ccgagcag                                                     18
```

<210> SEQ ID NO 8

<210> SEQ ID NO 8
<211> LENGTH: 64
<212> TYPE: DNA
<213> ORGANISM: Artificial Sequence
<220> FEATURE:
<221> NAME/KEY: primer_bind
<222> LOCATION: (1)..(64)
<223> OTHER INFORMATION: 5' oligonucleotide used for PCR amplification of Lox/NEO/URA3/Lox

<400> SEQUENCE: 8

```
atacttttttt ttttttcaga gacgtggagc tatttcctaa gaattccgat catattcaat    60
aacc                                                                  64
```

<210> SEQ ID NO 9
<211> LENGTH: 83
<212> TYPE: DNA
<213> ORGANISM: Artificial Sequence
<220> FEATURE:
<221> NAME/KEY: primer_bind
<222> LOCATION: (1)..(83)
<223> OTHER INFORMATION: lox oligonucleotide, used for PCR amplification of Lox/NEO/URA3/Lox

<400> SEQUENCE: 9

```
cttaatataa cttcgtataa tgtatgctat acgaagttat taggtctgaa gaggagttta    60
cgtccagctg cgcataaaaa tca                                             83
```

<210> SEQ ID NO 10
<211> LENGTH: 101
<212> TYPE: DNA
<213> ORGANISM: Artificial Sequence
<220> FEATURE:
<221> NAME/KEY: primer_bind
<222> LOCATION: (1)..(101)
<223> OTHER INFORMATION: 3' oligonucleotide used for PCR amplification of Lox/NEO/URA3/Lox

<400> SEQUENCE: 10

```
ataacttcgt ataatgtatg ctatacgaag ttattaggtc cagcggcccc cactgcggta    60
tgctaggtaa gtacaacttt attgttttta ttaaatttat g                       101
```

<210> SEQ ID NO 11
<211> LENGTH: 68
<212> TYPE: DNA
<213> ORGANISM: Artificial Sequence
<220> FEATURE:
<221> NAME/KEY: primer_bind
<222> LOCATION: (1)..(68)
<223> OTHER INFORMATION: 3' oligonucleotide containing intron2 and exon2, used for PCR amplification of Lox/NEO/URA3/Lox

<400> SEQUENCE: 11

```
cataaattta ataaaaacaa taaagttgta cttacctagc ataccgcagt gggggccgct    60
ggacctaa                                                              68
```

<210> SEQ ID NO 12
<211> LENGTH: 107
<212> TYPE: DNA
<213> ORGANISM: Artificial Sequence
<220> FEATURE:
<221> NAME/KEY: primer_bind
<222> LOCATION: (1)..(107)
<223> OTHER INFORMATION: lox oligonucleotide after popout of Lox/NEO/URA3

<400> SEQUENCE: 12

```
cttaatataa cttcgtataa tgtatgctat acgaagttat taggtccagc ggccccact      60 gcggtatgct aggtaagtac aactttattg tttttattaa atttatg                   107

<210> SEQ ID NO 13
<211> LENGTH: 171
<212> TYPE: DNA
<213> ORGANISM: Artificial Sequence
<220> FEATURE:
<221> NAME/KEY: primer_bind
<222> LOCATION: (1)..(171)
<223> OTHER INFORMATION: nucleic acid sequence of PDE7A locus after
      Cre-recombinase-mediated removal of Lox/NEO/URA3 sequence

<400> SEQUENCE: 13
atactttttt ttttttcaga gacgtggagc tatttcctaa gaattccgat catattcaat     60 aaccctaat ataacttcgt ataatgtatg ctatacgaag ttattaggtc cagcggcccc    120
cactgcggta tgctaggtaa gtacaacttt attgttttta ttaaatttat g             171

<210> SEQ ID NO 14
<211> LENGTH: 1330
<212> TYPE: DNA
<213> ORGANISM: Mus sp.
<220> FEATURE:
<221> NAME/KEY: variation
<222> LOCATION: (1)..(1330)
<223> OTHER INFORMATION: 'n' at positions 122, 963, 1262, and 1299 may
      be any nucleotide

<400> SEQUENCE: 14
gccgtggatc tgagagcatg ggtttggaac tcacttccca gacagtggga ccactggagg    60
acttgtgagt gggacctgaa atagccactc ctctaaggcc tggggcttgg ggaagatgca   120
cntgaaccat caacagattg gcctttcccc tctcgttccc tttgagtaac tcttgcgatt   180
gttttagaaa ccaacttcgg tggggctggg gatactgtgc caaagactcc agttccatcc   240
tcagcacccc actccacaga agagatcagc tgtgtgccat ctcagacgct tcactcctgt   300 gtcctttct taggagttct tagctaggtt gtacctgttt gtctcgtagc tagagatttc    360
cagagcagat gcattttgta tattcaacat tgtttggtgc aatatgctgc aattacatgt   420
aataatacaa gcatgttcac tgaattaaat tttagctcac atttcattat catgtactga   480
aatatatact tttttttttt tcagagacgt ggagctattt cctatgacag ttctgatcag   540
tctgcgttat atattcgtat gctaggtaag tacaacttta ttgttttat taaatttatg    600 tatatgagtt cacagatggt tgtgagcctt cacgtggttg ttgggaattg aatttaggac   660
ctctgctcac tccagtcaac tccgctcgct cagtccctac ttgctcaggc caaagatt     720 atttattatt ataaataagt acactcttgc tgtcttcaga cgcaccagaa gagggtgtca   780
gatctcatta tgggtggtta tgaaccacca tgtggttgct aggatttgaa ctcaggacct   840
tcagaagagc agtcagtgag tgctctttcc cactgagcca tctctccagc ccctaagtaa   900
aactttatac cagtaccagt tagtcttgcg gttgtattat ctgagatgag atatcttgca   960
ctnaggtacc tttcactact ttttgaagca gaaattgaag tttagcatct gaaaactaat  1020
actgagtgtg atgaataaag agaggtattt tagagttagg gcaatttaaa agtctggttt  1080
aataggacag tcttttaggg gacagcttag ctgttttaga gcattcttta tggaacatag  1140
gttaaatagg tttctaacac tgctaaaggc caaccaactg ctagttagct gtgcatacca  1200
cagtgtgtaa aatgaattat tttaatataa aatgtaagta ataaaattaa tccagcagct  1260
gnattccctt tacctttgct agtccccagt aatcacacng agaattccag acttatttca  1320
```
agctttccct                                                                  1330

<210> SEQ ID NO 15
<211> LENGTH: 868
<212> TYPE: DNA
<213> ORGANISM: Mus sp.
<220> FEATURE:
<221> NAME/KEY: variation
<222> LOCATION: (1)..(868)
<223> OTHER INFORMATION: 'n' at positions 8, 11, 15, 22, 24, 28, 33, 43,
      46, 47, 49, 71, 73, 121, 122, 129, 160, 219, 220, 242, 287, 312,
      317, 438, 445, 448, 473, 487, 514, 517, 548, 549, 576, 578, 585,
      594, 602, 604, 607, 638, 732, 740, 752, 757, 758, 780, 788, 812,
      826, and 842 may be any nucleotide

<400> SEQUENCE: 15 tacccccgnac ngcanttgcc tncngacngt gancagctga ctnttnngng aatgcactgc         60
ctggctagcc ntnctgccca gcgcatgctt aatgccacga cctcaccact agtgcaaagc        120
nngagaaana gtactggaag acaagaaaaa tctagcttan aatctcacaa aaggtctcag        180
gctagcccaa acatgcctgt gatctttgtt ctacagagnn ttttaaaaca attatcaaaa        240
angcttggca aggctaaaca tttcctcatc ctgctcacgg aggccantt tgcaagcata         300 attgccattg cnctccnaaa atatttgaac attttgcact ttacctctga gtattgaatt        360
tctttaaact tttgctttct tccaatatgg gattacttta tgacaacagt ggcacgataa        420
atgtgatctg tgccattnaa atacntangt aattcattct aaatttactg acnaggtcat        480
gtattancac ataataaaag atattttgtt ctcnagncct aagaaagtct aaggtcctgt        540
aatattanng gtccatgtcc tgttcttgcg actgancnga atgancttgt ccanaaacaa        600
angnctntcc gtatcccaac ctcttacctt ccattggnaa cccaagcaag ttacttttga        660
taaaagagcc tctcacgaaa cctctcaatc gagaagttag caaatatgtt tttaaactct        720
attacccagc angctccatn ttaatgacaa anaattnnct aaaaaatcat agtgatccgn        780
aacctggntt cctgcccttt atacaattt tnttccatat taaccnaatg gtgcaacaaa        840
tnccaaattg gcttgaacgg gaaaagga                                           868